Figure 1:
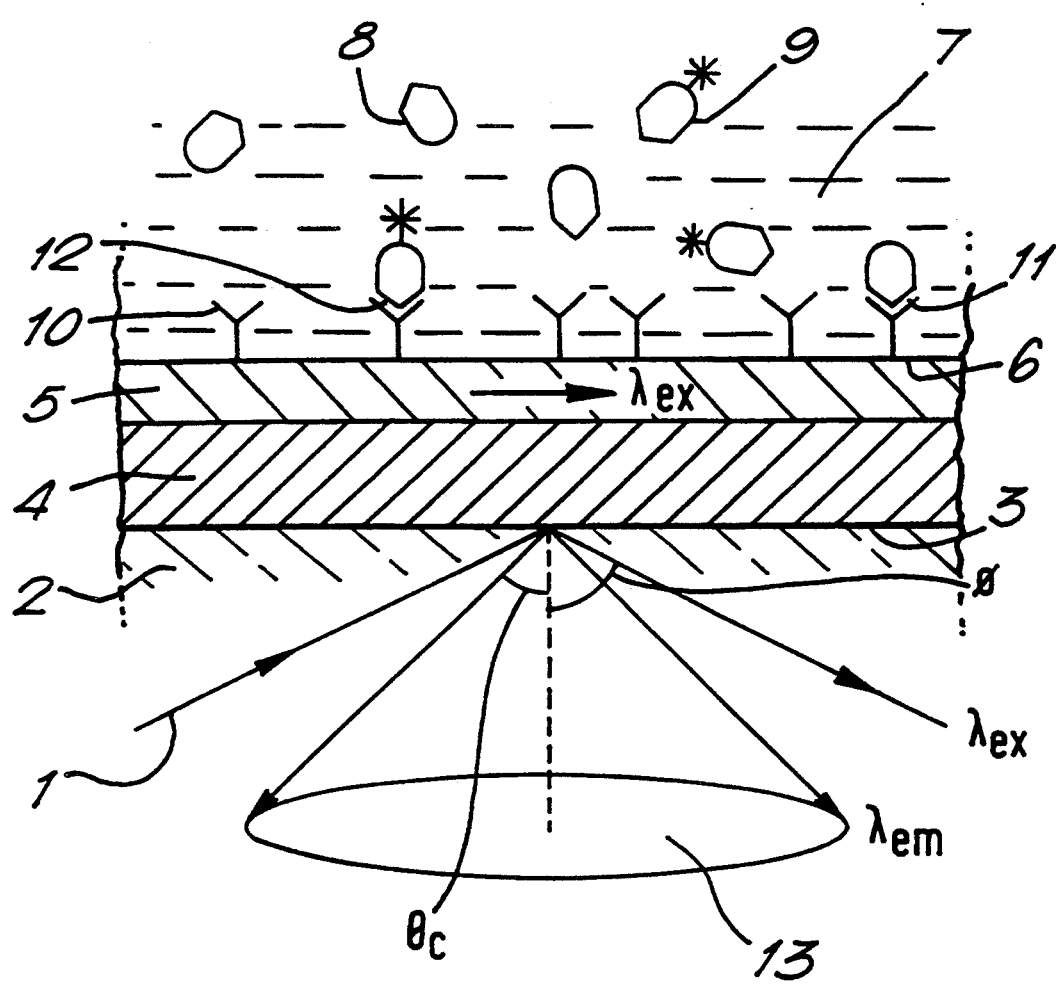

United States Patent [19]
Attridge

[11] Patent Number: 5,344,784
[45] Date of Patent: Sep. 6, 1994

[54] FLUORESCENT ASSAY AND SENSOR THEREFOR

[75] Inventor: John W. Attridge, Woking Surrey, United Kingdom

[73] Assignee: Applied Research Systems ARS Holding N.V., Netherlands

[21] Appl. No.: 689,850

[22] PCT Filed: Nov. 28, 1989

[86] PCT No.: PCT/GB89/01420
 § 371 Date: May 21, 1991
 § 102(e) Date: May 21, 1991

[87] PCT Pub. No.: WO90/06503
 PCT Pub. Date: Jun. 14, 1990

[30] Foreign Application Priority Data

Nov. 29, 1988 [GB] United Kingdom ............... 8827853

[51] Int. Cl.$^5$ .................................... G01N 33/552
[52] U.S. Cl. .................................... 436/518; 385/12;
 385/129; 385/130; 385/131; 422/55; 422/57;
 422/58; 422/82.05; 422/82.08; 435/808;
 436/172; 436/524; 436/525; 436/527; 436/537;
 436/805; 436/807
[58] Field of Search ............... 385/129–131,
 385/12; 250/364, 368, 483.1, 487.1; 422/55, 57,
 58, 82.05, 82.08; 436/518, 524, 525, 527, 172,
 805, 807, 537, 800; 435/808

[56] References Cited

U.S. PATENT DOCUMENTS

| 3,563,630 | 2/1971 | Anderson et al. | 385/130 |
| 3,806,223 | 4/1974 | Kech et al. | 385/129 |
| 3,873,339 | 3/1975 | Hudson | 385/129 |
| 3,874,782 | 4/1975 | Schmidt | 385/8 |
| 4,174,384 | 11/1979 | Ullman et al. | 436/800 |
| 4,277,437 | 7/1981 | Maggio | 436/800 |
| 4,318,707 | 3/1982 | Litman et al. | 436/537 |
| 4,329,016 | 5/1982 | Chen | 385/129 |
| 4,582,809 | 4/1986 | Block et al. | 436/527 |
| 4,649,280 | 3/1987 | Holland et al. | 250/368 |
| 4,774,191 | 9/1988 | Khanna et al. | 436/518 |
| 4,857,273 | 8/1989 | Stewart | 422/55 |

FOREIGN PATENT DOCUMENTS

0072627 2/1983 European Pat. Off. .
0170376 2/1986 European Pat. Off. .
0171148 2/1986 European Pat. Off. .
8706956 11/1987 PCT Int'l Appl. .

Primary Examiner—Toni R. Scheiner
Assistant Examiner—Christopher L. Chin
Attorney, Agent, or Firm—Ostrolenk, Faber, Gerb & Soffen

[57] ABSTRACT

The invention relates to a device for use in optical methods of assay. The device comprises an optical structure comprising a dielectric substrate (2) and a thin film waveguide (5), between which is interposed a buffer layer (4). The waveguide carries a layer (10) of reagent suitable for a desired assay. The invention also relates to methods of using the device in an assay.

14 Claims, 1 Drawing Sheet

FLUORESCENT ASSAY AND SENSOR THEREFOR

This invention relates to a device for the enhancement of fluorescence and in particular to a device for use in fluorometric systems and methods for the assay of chemical or biochemical entities.

Methods of assay involving the use of fluorescence biosensors and employing evanescent wave coupling techniques are known, see for example EP-A-170376. The present invention provides means for carrying out assays employing evanescent wave coupling techniques whereby an improved signal-to-noise ratio and enhanced sensitivity may be obtained.

U.S. Pat. No. 4,649,280 describes a device for enhancing fluorescence comprising a waveguide defined by a dielectric layer of predetermined thickness having layers of fluorescent and of conductive material on opposite surfaces of the said layer. The present invention avoids the need for a conductive layer, thereby reducing the cost of materials and increasing the ease of fabrication of the device. The invention also allows greater design flexibility in producing sensors and allows a greater range of wavelengths of light to be used. Furthermore, methods according to the present invention are not polarisation dependant.

According to the present invention there is provided a sensor device for use in assaying chemical or biochemical substances by optical methods which sensor comprises an optical structure comprising:

(a) a dielectric substrate transparent at least at the wavelengths of radiation involved in the assay;

(b) a thin film waveguide of dielectric material having a refractive index higher than that of the substrate, the waveguide carrying a layer (continuous or discontinuous) of a reagent appropriate to the assay to be carried out, the said reagent being immobilized directly or indirectly on the surface of the waveguide remote from the substrate; and (c), interposed between (a) and (b), a buffer layer of dielectric material of refractive index lower than that of the substrate; the thicknesses of the buffer layer and the waveguide being such that, in use, one or more guided modes may be propagated within the waveguide.

In a preferred embodiment, the thicknesses of the buffer layer and the waveguide are such that a single transverse magnetic (TM) and/or single transverse electric (TE) guided mode may be propagated within the waveguide.

A practical advantage accruing from use of an optical structure containing no metal layers is that fabrication of such devices is possible without the need for vacuum evaporation techniques; for example, spun-coated phosphate glasses may be used.

Furthermore, using a given combination of refractive indices of substrate, buffer layer, waveguide and solution it is possible in principle to design a device wherein the evanescent field is more highly confined than in previously known devices. When the device is used in fluorometric methods of assay this therefore leads to better discrimination between fluorophores bound to the surface of the device and fluorophores in solution. Additionally, the intensity of the evanescent field is enhanced resulting in greater excitation of the fluorophores within the evanescent field thereby improving the intensity of the emitted light compared to previously known devices.

Suitable materials for the substrate include glass, acrylic and polystyrene plastics, silica and quartz; suitable materials for the buffer layer include any material of suitably low refractive index which can be formed as an optically transparent thin film, such as magnesium fluoride, lithium fluoride, silicon dioxide and phosphate glasses; suitable materials for the waveguide layer include any material of suitably high refractive index which can be formed as an optically transparent thin film, such as zinc sulphide, zinc selenide, phosphate glasses lithium niobate, tin oxide and suitable polymers, e.g. polystyrene.

Preferably the buffer layer is 0.1 to 2 microns thick (for example, a buffer layer of $SiO_2$ may be 0.6 microns thick and a buffer layer of $MgF_2$ may be 0.7 microns thick) and the waveguide layer is 0.16 to 1.0 microns thick (for example, a waveguide layer of tin oxide may be 0.32 microns thick and a waveguide layer of ZnS may be 0.2 microns thick)- The thickness of the substrate layer is not critical to the working of the sensor.

For maximum efficacy, the interfaces between the various layers of the sensor device should be smooth and parallel.

The sensors of the present invention are particularly suitable for use in methods of assay which are based on the affinity between the species which is to be assayed (hereinafter called "ligand") and a specific binding material for the ligand (hereinafter called "specific binding partner"). More particularly, the sensors of the invention can be used in assays involving measurement of fluorescence emitted by a fluorophore conjugated with an appropriate reagent.

The reagent appropriate to the assay to be carried out may be a specific binding partner for the ligand under assay or may be a ligand analogue. Examples of such entities are given later.

The sensors of the invention are also of use in assays involving measurement of absorption by a chromophore conjugated with an appropriate reagent.

According to a further feature of the present invention there is provided a method of using a sensor as hereinbefore defined to assay for a ligand in a sample which method includes the steps of:

(a) incubating, simultaneously or in any desired sequence, (i) the sample (ii) a specific binding partner to the ligand and (iii) if desired, at least one further reagent selected from specific binding partners and ligand analogues one of the above components (other than the sample) being the reagent immobilized directly or indirectly on the waveguide surface of the said sensor; and at least one of the above components (other than the sample) being labelled with a fluorophore or a chromophore;

(b) irradiating a surface of the substrate of the said sensor with light of an appropriate wavelength at a suitable angle to the normal such that total internal reflection occurs at the interface between the substrate and the buffer layer of said sensor and whereby the evanescent field associated therewith gives rise to propagation of one or more guided modes in the waveguide layer of said sensor; and (c) determining whether and, if desired, the extent to which and/or rate at which an appropriate optical property of radiation emerging from said sensor is altered by complex formation. The optical property of the light measured at a given angle to the plane of said sensor may be, for example, wavelength, intensity or polarization.

The alteration in the appropriate optical property can, for example, be determined in accordance with step (c) with reference to a separate calibration step, or by incubating different zones of the device with sample and reference solution(s) respectively.

The term "ligand analogue" as used herein means a species which will bind specifically to the same binding site of the same specific binding partner as will the ligand and includes within its scope ligand molecules distinguishable from the ligand itself.

When the component (ii) (or one of components (ii) and (iii)) is labelled with a fluorophore, the radiation of step (c) will be fluorescence radiation.

In a method of assay according to the invention involving measurement of absorption by a chromophore conjugated with an appropriate reagent, the assay and reagents used will be similar to the fluorometric assays described above except that component (ii) (or one of components (ii) and (iii)) will be labelled with the chromophore instead of with a fluorophore and it will be an appropriate optical property of the reflected beam of radiation of the excitation wavelength which is monitored during the assay. The invention will hereinafter be described with reference to fluorometric methods of assay.

Where component (iii) is absent, then the reagent immobilized directly or indirectly on the waveguide surface of the sensor will be a specific binding partner labelled with a fluorophore. The reagent and fluorophore will be chosen such that on complex formation with any ligand present in the sample, quenching of fluorescence occurs such that there is a decrease in intensity of fluorescence radiation.

Where component (iii) is present, then one of components (ii) and (iii) will be the reagent immobilized directly or indirectly on the waveguide surface of the sensor, denoted herein as reagent Y for convenience, the other of components (ii) and (iii) being denoted herein for convenience as reagent X. Where one of the reagents X and Y comprises a ligand analogue and the other of reagents X and Y comprises a specific binding partner to the ligand, complex formation between reagents X and Y may occur directly. Alternatively, where both reagents X and Y comprise specific binding partners to the ligand, complex formation between reagents X and Y indirectly via the ligand, if present in the sample, may occur. In general, it will be reagent X which is labelled with the fluorophore and, as a result of complex formation, the fluorophore present as a label on reagent X becomes indirectly bound to the waveguide surface.. However, if it is reagent Y which is labelled with fluorophore then with an appropriate choice of reagents and fluorophore, quenching of fluorescence can occur on complex formation.

Although the order of incubation is not critical when component (iii) is present, it is preferred that the complex is formed after introduction of the final component but not prior thereto. It is, however, alternatively possible for there to be complex present before the final component is added, in which case the final component will become complexed by displacing one component of the pre-existing complex. Where the final component is the sample and the component labelled with fluorophore is a ligand analogue, a displacement of ligand analogue by any ligand present in the sample will then result in a decrease in intensity of fluorescence radiation.

As mentioned above, reagent Y may be either directly or indirectly immobilized on the surface of the waveguide layer. For example, when reagent Y is an antibody, indirect immobilization may be effected by means of an anti-species antibody to reagent Y which is itself bound to the surface of said waveguide layer; alternatively indirect immobilization may be effected by means of avidin/biotin or hapten/anti-hapten systems.

The technique of the present invention makes it possible to maximise the response to complex formation at the surface of the sensor and when employed in fluorometric methods of assay significantly reduces the background signals arising from unbound fluorophore and from solution fluorescence.

In the sensors according to the present invention, the buffer layer and the waveguide layer will in general both have a thickness of the order of the wavelength of the incident radiation used. In particular, as mentioned previously, the waveguide should be of a suitable thickness to support one or more guided modes but it is particularly preferred to employ a thickness of waveguide material which will support only a single guided TE or TM mode. For example, for a substrate of refractive index 1.52 (e.g. crown glass) with a buffer layer of $SiO_2$ of thickness 0.6 micron and refractive index 1.46, and an incident radiation of wavelength 580 nm, the thickness of a waveguide layer of $SnO_2$ suitable for propagation of guided TE or TM modes therein is approximately from 0.16 microns to 0.3 microns. Alternatively, for a substrate of crown glass (refractive index 1.52) with a buffer layer of $MgF_2$ of thickness 1 micron and refractive index 1.38 and an incident radiation of wavelength 580 nm, the thickness of a waveguide layer of ZnS suitable for propagation of guided TE or TM modes therein is approximately 0.16 microns to 0.33 microns. It is important that the waveguide material has a high refractive index relative to that of the sample (e.g. 2.0 for $SnO_2$; 2.36 for ZnS) in order that guiding can occur in a thin waveguide to maximise the excitation energy within the evanescent field.

The optics of the method of the present invention will now be discussed with reference to FIG. 1 which is a schematic illustration of one possible sensor of the present invention in use.

For simplicity, the lower boundary of the substrate layer (and any refraction of light which would occur thereat) is not shown. Radiation (1) of a suitable wavelength $\lambda_{ex}$ is applied to the sensor through the substrate (2) such that it impinges on the interface (3) between the substrate (2) and the buffer layer (4) at an angle $\Phi$ greater than the critical angle $\theta_c$ between these layers, i.e. such that the exciting radiation is totally internally reflected and the evanescent field penetrates the buffer layer (4). As a consequence of evanescent coupling, radiation of the excitation wavelength $\lambda_{ex}$ is propagated within the high index waveguide (5). With an appropriate choice of refractive indices and thicknesses for the substrate, buffer layer and waveguide layer, a significant enhancement of the evanescent field intensity is possible at the interface (6) of the waveguide and the sample solution (7). During the course of the particular type of assay illustrated by FIG. 1, free ligand molecules (8) and fluorescent ligand analogue molecules (9) in the solution compete for a particular binding site of a mutual specific binding partner (10) bound to the waveguide surface. As a result, complexes (11 and 12) are formed at the waveguide surface, some of which will contain fluorophores. The evanescent field decays exponentially away from the surface of the waveguide layer. Consequently, only fluorescently labelled molecules within the evanescent field at the waveguide surface become excited and fluoresce, thus achieving a discrimination between fluorophore bound to the surface as a result of the assay and the unbound fluorophore in solution. The fluorescence emission is markedly more intense than can be achieved by direct illumination using the same light source. A proportion of the fluorescence emission will couple back through the system in a known manner, to give a narrow angle cone (13) of emission of wavelength $\lambda_{em}$ in the substrate, the angular distribution of which will depend on the waveguide dispersion and the fluorescence emission spectrum. The resulting enhanced narrow angle fluorescence emission can be measured in a known manner. The cone of emission shown in FIG. 1 is entirely schematic.

Enhanced fluorescence radiation is also emitted into the sample solution; the optical properties of this may also be measured. Alternatively, by a suitable arrangement of apparatus, detection of light emerging from an edge of the substrate or waveguide layer of said sensor may also be employed.

The present invention further provides apparatus suitable for use in the method of assay hereinbefore described which comprises a collimated source of radiation arranged such that, in use, light enters a sensor as described-herein at an angle suitable to produce total internal reflection within the optical structure and means to detect the emergent fluorescence radiation. The exciting radiation may be collimated, for example, to within one or two degrees and may, in use, be introduced into a sensor within said apparatus, for example, through an edge of the substrate of the sensor or via a prism or a grating coupler. Ideally, the incident radiation is polarized, but unpolarized incident radiation may also be used.

According to a still further feature of the present invention there is provided a kit for use in an assay as described above, the said kit comprising a sensor according to the invention as hereinbefore defined together with one or more reagents appropriate to the assay to be carried out. The reagents may be selected from specific binding partners and ligand analogues.

It is preferred to apply the method of the invention to an immunoassay and in particular to use a specifically-reactive sample collecting and testing device similar to that described in EP-0171148. Thus, the present invention provides a device having a cavity or cavities each having a dimension small enough to enable sample liquid to be drawn into the cavity by capillary action, and wherein at least one part of a wall of said cavity comprises a sensor for detecting a ligand in said sample as defined hereinbefore. In this particular embodiment of the invention the substrate itself comprises a planar waveguide.

The method of the invention is particularly applicable to assays of antigens or antibodies, i.e. to immunoassays and in a preferred embodiment of the invention the ligand is an antigen and the specific binding partner comprises an antibody to the said antigen. However, the invention is not to be taken as limited to assays of antibodies or antigens. As mentioned above, a reagent immobilized on the waveguide surface of a sensor according to the present invention will be either a specific binding partner to the ligand under assay or a ligand analogue. Examples of ligands which may be assayed by the method of the invention are given in Table 1 below, together with an indication of a suitable specific binding partner in each instance.

TABLE 1

| Ligand | Specific Binding Partner |
| --- | --- |
| antigen | specific antibody |
| antibody | antigen |
| hormone | hormone receptor |
| hormone receptor | hormone |
| polynucleotide strand | complementary polynucleotide strand |
| avidin | biotin |
| biotin | avidin |
| protein A | immunoglobulin |
| immunoglobulin | protein A |
| enzyme | enzyme cofactor (substrate) or inhibitor |
| enzyme cofactor (substrate) or inhibitor | enzyme |
| lectins | specific carbohydrate |
| specific carbohydrate of lectins | lectins |

The method of the invention has very broad applicability but in particular may be used to assay: hormones, including peptide hormones (e.g. thyroid stimulating hormone (TSH), luteinizing hormone (LH), human chorionic gonadotrophin (hCG), follicle stimulating hormone (FSH), insulin and prolactin) or non-peptide hormones (e.g. steroid hormones such as cortisol, estradiol, progesterone and testosterone, or thyroid hormones such as thyroxine (T4) and triiodothyronine), proteins (e.g. carcinoembryonic antigen (CEA) and alphafetoprotein (AFP)), drugs (e.g. digoxin or drugs of abuse), sugars, toxins, vitamins, proteins, viruses such as influenza, para-influenza, adeno-, hepatitis, respiratory and AIDS viruses, or microorganisms.

It will be understood that the term "antibody" used herein includes within its scope:

(a) any of the various classes or sub-classes of immunoglobulin, e.g. IgG, IgA, IgM, or IgE derived from any of the animals conventionally used, e.g. sheep, rabbits, goats or mice, (b) monoclonal antibodies, (c) intact molecules or "fragments" of antibodies, monoclonal or polyclonal, the fragments being those which contain the binding region of the antibody, i.e. fragments devoid of the Fc portion (e.g. Fab, Fab', F(ab')$_2$) or the so-called "half-molecule" fragments obtained by reductive cleavage of the disulphide bonds connecting the heavy chain components in the intact antibody.

The method of preparation of fragments of antibodies is well known in the art and will not be described herein.

The term "antigen" as used herein will be understood to include both permanently antigenic species (for example, proteins, bacteria, bacterial fragments, cells, cell fragments and viruses) and haptens which may be rendered antigenic under suitable conditions.

Examples of fluorescent molecules which may be used to label the ligand conjugate are fluorescein isothiocyanate (FITC), rhodamine isothiocyanate, 2,4-dinitrofluorobenzene, phenylisothiocyanate and dansyl chloride, substituted rhodamine isothiocyanates (XRITC), tetramethyl/rhodamine isothiocyanate (TRITC) codaverine (TRAP) and phycobiliproteins (e.g. allophycocyanin and phycoerythrin).

The following non-limiting Examples illustrate the construction of sensors in accordance with the invention and assays using such sensors.

EXAMPLE 1

Construction of Sensors

A suitable substrate material (e.g. crown glass, refractive index 1.52) is cleaned and a buffer layer of silicon dioxide (refractive index 1.46), 0.6 microns thick, is deposited onto the glass substrate by vacuum evaporation techniques known in the art. A layer of tin (IV) oxide (refractive index 2.0), 0.3 microns thick, is then deposited onto the magnesium fluoride, also by vacuum evaporation. The layer of tin (IV) oxide is to act as the waveguide part of the sensor.

Antibody specific for the antigen of interest is immobilized on the surface of the waveguide, either by adsorption or by covalent coupling using techniques known in the art.

An alternative structure would comprise a magnesium fluoride buffer layer (refractive index 1.38), 0.7 microns thick, and a tin oxide waveguide, 0.25 microns thick.

Alternative materials for the waveguide are zinc sulphide (refractive index 2.36) as a layer 0.2 microns thick, which can be deposited onto the magnesium fluoride layer by vacuum evaporation; and an indium phosphate glass (refractive index 1.61) as a layer 0.5 microns thick, which can be deposited onto the magnesium fluoride layer by spin coating. The refractive indices of indium phosphate glasses can be precisely controlled (see Sloper and Flanagan, Electronics Letters 24 (1988))

The embodiments described in this Example are each capable of enhancing the electric field intensity at the surface of the waveguide by up to 260 times, when used in a method according to the invention, compared with a method employing direct illumination of the surface.

EXAMPLE 2

Use of a Sensor of Example 1 in an Assay for an Antigen

The appropriate surface of a sensor as described in Example 1 is incubated with sample liquid and (simultaneously or sequentially) with fluorescently labelled antigen or a fluorescently labelled second antibody specific for the antigen of interest, depending upon the chosen assay methodology. As a result, if the antigen under assay is present in the sample, immunocomplexes are formed on the waveguide surface of the sensor, whereby fluorophores become bound to the waveguide surface.

A surface of the substrate is irradiated at a suitable wavelength and angle to excite a guided mode within the waveguide. Any fluorophores within the evanescent field at the waveguide surface are excited by the enhanced evanescent wave associated with this guided mode. Preferred sources of radiation are of monochromatic and/or polarised light (e.g. from a laser).

Fluorescence radiation which is emitted is monitored. Light emerging from the sensor is collected by the detection optics and any light of the excitation wavelength is preferably filtered out before the intensity measurement is made. The fluorescent light emerging from the substrate which originates from any fluorophores bound to the waveguide surface has a distinct angular distribution (see FIG. 1). The operating signal-to-noise ratio of the sensor is thus very low, particularly when the radiation source is polarized.

The detection optics will consist of a photodetector (either a photomultiplier tube or a solid state detector) with, optionally, some filtration to remove light of excitation wavelength; examination of the polarisation of the light may be beneficial and may therefore optionally be performed. Use of an aperture also facilitates ease of detection.

In an alternative method of assay according to the invention, the fluorophores may be excited by direct illumination, either through the substrate or through the sample, such that the emitted light is collected via the guided modes of the device. In this embodiment, which is analogous to the method described in EP-170376, the enhanced intensity of the evanescent field is lost but the signal to noise ratio of the device is improved via the reduced angular distribution of the emitted light which allows for increased efficiency of collection and measurement. According to a further feature of the present invention there is thus provided a kit for use in a method of assay as described above comprising a sensor as described above together with one or more reagents appropriate to the said method.

I claim:

1. A method of assaying for a ligand in a sample which comprises:
    (A.) incubating, simultaneously or in any desired sequence,
        (i) the sample, and
        (ii) a specific binding partner to the ligand,
    wherein reagent (ii) is labelled with a fluorophore and is immobilised directly or indirectly on a waveguide surface of an optical structure comprising:
        (a) a dielectric substrate transparent at least at wavelengths of radiation involved in the assay;
        (b) a thin-film waveguide of dielectric material having a refractive index higher than that of the substrate; and
        (c) interposed between (a) and (b), a buffer layer of dielectric material having a refractive index lower than that of the substrate, wherein the buffer layer and the waveguide each are of a thickness such that, when said optical structure is in use, one or more guided modes may be propagated within the waveguide;
    (B.) irradiating a surface of the optical structure's substrate with light of an appropriate wavelength at a suitable angle to the normal such that total internal reflection occurs at the interface between the substrate and the buffer layer of said optical structure and whereby an evanescent field associated therewith gives rise to propagation of one or more guided modes in the waveguide of said optical structure, and such that floroescence arising from excitation of bound fluorophore within said evanescent field and which couples back into the substrate leaves the interface between the buffer layer and the substrate at angles to the normal which are less than the critical angle at the interface; and
    (C.) determining whether an optical property of floroescence emerging from said optical structure is altered by formation of immunocomplexes on the waveguide, whereby the alteration in optical property of fluorescence is related to the presence of ligand in the sample.

2. A method as claimed in claim 1 wherein the extent to which or the rate at which, or both, the optical property of fluorescence emerging from said optical structure is altered by formation of immunocomplexes on the waveguide is determined.

3. A method of assaying for a ligand in a sample which comprises:
   (A.) incubating simultaneously or in any desired sequence,
       (i) the sample,
       (ii) a specific binding partner to the ligand, and
       (iii) a reagent selected from the group consisting of a specific binding partner to the ligand and a ligand analogue,
   wherein at least one of the above reagents (ii) or (iii) is labelled with a fluorophore and one of the above reagents (ii) and (iii) is immobilised directly or indirectly on a waveguide surface of an optical structure comprising:
       (a) a dielectric substrate transparent at least at wavelengths of radiation used in the assay;
       (b) a thin-film waveguide of dielectric material having a refractive index higher than that of the substrate; and
       (c) interposed between (a) and (b), a buffer layer of dielectric material having a refractive index lower than that of the substrate, wherein the buffer layer and the waveguide each are of a thickness such that, when said optical structure is in use, one or more guided modes may be propagated within the waveguide;
   (B.) irradiating a surface of the optical structure's substrate with light of an appropriate wavelength at a suitable angle to the normal such that total interest reflection occurs at the interface between the substrate and the buffer layer of said optical structure and whereby an evanescent field associated therewith gives rise to propagation of one or more guided modes in the waveguide of said optical structure, and such that fluorescence arising form excitation of bound fluorophore within said evanescent field and which couples back into the substrate leaves the interface between the buffer layer and the substrate at angles to the normal which are less than the critical angle at the interface; and
   (C.) determining whether an optical property of fluorescence emerging from said optical structure is altered by formation of immunocomplexes on the waveguide, whereby the alteration in optical property of fluorescence is related to the presence of ligand in the sample.

4. A method as claimed in claim 3 wherein the extent to which or the rate at which, or both, the optical property of fluorescence emerging from said optical structure is altered by formation of immunocomplexes on the waveguide is determined.

5. A method as claimed in claim 3 wherein reagent (iii) is a ligand analogous possessing a fluorophore as a label.

6. A method as claimed in claim 5 wherein the extent to which or the rate at which, or both, the optical property of fluorescence emerging from said optical structure is altered by formation of immunocomplexes on the waveguide is determined.

7. A method as claimed in claims 1 or 3 wherein the ligand is an antigen and the specific binding partner comprises an antibody to said antigen.

8. A method as claimed in claim 7 wherein the extent to which or the rate at which, or both, the optical property of fluorescence emerging from said optical structure is altered by formation of immunocomplexes on the waveguide is determined.

9. An assay sensor which comprises an optical structure comprising:
   (a) a dielectric substrate;
   (b) a thin-film waveguide of dielectric material having a refractive index higher than that of the substrate; and
   (c) interposed between (a) and (b), a buffer layer of dielectric material having a refractive index lower than that of the substrate,
   said optical structure having immobilised directly or indirectly on a surface of the waveguide remote from the substrate a continuous or discontinuous layer of a reagent appropriate to an assay to be carried out using said optical structure, wherein the buffer layer and the waveguide each are of a thickness such that, when said optical structure is in use, one or more guided modes may be propagated within the waveguide, and such that fluorescence arising from excitation of any fluorophore which, in use, is within an evanescent field associated with the optical structure and which fluorescence couples back into the substrate leaves the interface between the buffer layer and the substrate at angles to the normal which are less than the critical angle at the interface.

10. A sensor as claimed in claim 9 wherein the thicknesses of the buffer layer and the waveguide are such that, in use, a single transverse magnetic (TM) and/or transverse electric (TE) guided mode may be propagated within the waveguide.

11. A sensor as claimed in claim 9 wherein the buffer layer has a thickness between 0.1 and 2.0 microns and the waveguide has a thickness of between 0.16 and 1.0 microns.

12. A sensor as claimed in claim 11 wherein the buffer layer is silicon dioxide and has a thickness of about 0.6 microns and the waveguide is tin oxide and has a thickness of about 0.3 microns.

13. A sensor as claimed in claim 11 wherein the buffer layer is magnesium fluoride and has a thickness of about 0.7 microns and the waveguide is zinc sulphide and has a thickness of about 0.2 microns.

14. A specifically reactive sample collecting and testing device possessing a cavity or cavities each having a dimension small enough to enable sample liquid to be drawn into the cavity by capillary action, and wherein at least one part of a wall of said cavity comprises a sensor as claimed in claim 9.

* * * * *